United States Patent [19]
Martell et al.

[11] Patent Number: 5,610,966
[45] Date of Patent: Mar. 11, 1997

[54] METHOD AND DEVICE FOR LINEAR WEAR ANALYSIS

[75] Inventors: John M. Martell, Hinsdale; Sunjay Berdia, Chicago, both of Ill.

[73] Assignee: Argonne National Laboratories/University of Chicago Development Corp., Chicago, Ill.

[21] Appl. No.: 388,698

[22] Filed: Feb. 15, 1995

[51] Int. Cl.$^6$ .................................................. G01N 23/04
[52] U.S. Cl. ................................ 378/58; 378/54; 378/901
[58] Field of Search ........................ 364/413.13, 413.14; 128/653.1; 378/54, 56, 58, 901

[56] References Cited

U.S. PATENT DOCUMENTS

| | | | |
|---|---|---|---|
| 4,123,806 | 11/1978 | Amstutz et al. | 623/22 |
| 4,277,828 | 7/1981 | Tateishi | 364/413.02 |
| 4,422,187 | 12/1983 | Zweymüller | 623/23 |
| 4,436,684 | 3/1984 | White | 264/138 |
| 4,822,368 | 4/1989 | Collier | 623/22 |
| 4,892,548 | 1/1990 | Niederer et al. | 623/22 |
| 5,007,936 | 4/1991 | Woolson | 623/23 |
| 5,024,239 | 6/1991 | Rosenstein | 128/774 |
| 5,099,859 | 3/1992 | Bell | 128/781 |
| 5,148,455 | 9/1992 | Stein | 378/55 |
| 5,172,695 | 12/1992 | Cann et al. | 128/653.1 |
| 5,272,760 | 12/1993 | Echerer et al. | 382/6 |
| 5,490,507 | 2/1996 | Wilk et al. | 128/653.1 |

OTHER PUBLICATIONS

Isaac GH, Atkinson JR, Dowson D, Kennedy PD, Smith MR, *The Causes of Femoral Head Roughening in Explanted Charnley Hip Prostheses*, Eng. Med., 1987; 16:167–73.

Schmalzried TP, Jasty J., Harris WH, *Periprosthetic Bone Loss in Total Hip Arthroplasty*, The Journal of Bone and Joint Surgery, Inc., 1992, 74–A:849–863.

Black J., *The Future of Polyethylene*, The Journal of bone and Joint Surgery, Inc., 1978; 60–B:303–6.

Howie DW., Vernon–Roberts B., Oakshott R., Manthey B., *A Rat Model of Resorption of Bone at the Cement–Bone Interface in the Presence of Polyethylene Wear Particles*, The Journal of Bone and Joint Surgery, Inc., 1988; 70–A:257–63.

Kim JK, chiba J., Rubash HE., *In Vivo and In Vitro Analysis of Membranes From Hip Prostheses Inserted Without Cement*, The Journal of Bone and Joint Surgery, Inc., 1994, 76–A:172–80.

Mirra JM., Marder RA., Amstutz HC., *The Pathology of Failed Total Joint Arthroplasty*, Clin Orthop., 1982; 170:175–183.

Revell PA., Weightman B., Freeman MA., Roberts BV., *The Production and Biology of Polyethylene Wear Debris*, Arch Orthop Trauma Surg., 1978; 91:167–81.

(List continued on next page.)

*Primary Examiner*—David P. Porta
*Assistant Examiner*—David Vernon Bruce
*Attorney, Agent, or Firm*—Welsh & Katz, Ltd.

[57] ABSTRACT

A method and apparatus are disclosed for non-invasively determining the wear of a liner separating a rotatable bearing from a generally spherical housing. The method includes digitizing a first radiographic image of the bearing and housing and processing elements making up the image to define and locate the centers of the bearing and housing within the image. The process is also undertaken for a second radiograph image of the bearing and housing taken earlier than the first radiograph. The movement of the center of the bearing relative to the center of the housing during the time period between the making the first radiographic image and the second radiographic image being related to the wear of the liner.

17 Claims, 4 Drawing Sheets

OTHER PUBLICATIONS

Isaac GH., Atkinson JR, Dowson D., Wroblewske BM., *The Role of Acrylic Cement in Determining the Penetration Rate of the Femoral Heads in the Polyethylene Sockets of Charnley Hip Prostheses*, In: Willer H–G, Buchhorn GH, Eyerer P, eds., Ultra–high Molecular Weight Polyethylene as a biomaterial in Orthopaedic Surgery, Toronto: Hogrefe & Huber, 1990.

Cates HE., Faris PM., Keating EM., Ritter MA., *Polyethylene Wear in Cemented Metal–Backed Acetabular Cups*, The Journal of Bone and Joint Surgery, Inc., 1993; 75–B:249–53.

Cooper RA., McAllister CM, Borden LS, Bauer TW, *Polyethylene Debris–Induced Osteolysis and Loosening in Uncemented Total Hip Arthroplasty. A Cause of Late Failure*, J. Arthroplasty, 1992, 7:285–90.

Maloney WJ, Jasty M, Harris WH, Galante JO, Callaghan JJ, *Endosteal Erosion in Association With Stable Uncemented Femoral Components*, The Journal of Bone and Joint Surgery, Inc., 1990: 72–A1025–1034.

Maloney WJ, Peters P, Engh CA, Chandler H, *Severe Osteolysis of the Pelvis in Association With Acetabular Replacement Without Cement*, The Journal of Bone and Joint Surgery, Inc., 1993; 75–A:1627–35.

Martell JM, Pierson RH, Jacobs JJ, Rosenberg AG, Maley M, Galante JO, *Primary Total Hip Reconstruction With A Titanium Fiber–Coated Prosthesis Inserted Without Cement*, The Journal of Bone and Joint Surgery, Inc., 1993, 75–A:554–571.

Schmalzried TP, Guttman D, Grecula M, Amstutz HC, *The Relationship Between the Design, Position, and Articular Wear of Acetabular Components Inserted Without Cement and the Development of Pelvic Osteolysis*, The Journal of Bone and Joint Surgery, Inc., 1994, 76–A:677–88.

Livermore J., Ilstrup D., Morrey B., *Effect of Femoral Head on Wear of the Polyethylene Acetabular Component*, The Journal of Bone and Joint Surgery, Inc., 1990;72–A:518–28.

Wroblewski BM, *Direction and Rate of Socket Wear in Charnley Low Friction Arthroplasty*, The Journal of Bone and Joint Surgery, Inc., 1985; 67–B:757.

Bankston AB, Faris PM, Keating M, Ritter MA, *Polyethylene Wear in Total Hip Arthroplasty in Patient–Matched Groups*, J. Arthroplasty, 1993; 8:315–22.

Hardinge K, Porter ML, Jones, PR, Hukins DWL, Taylor CJ, *Measurement of Hip Prostheses Using Image Analysis: The Maxima Hip Technique*, The Journal of Bone and Joint Surgery, Inc., 1991; 73–B:724–8.

Jones PR, Taylor CJ, Hukins DWL, Porter ML, Hardinge K, *Prosthetic Hip Failure: Retrospective Radiograph Image Analysis of the Acetabular Cup*, J. Biomed Eng., 1989; 11:253–57.

Ballard DH, Brown CM, *Computer Vision*, Englewood Cliffs, new Jersey: Prentice–Hall 1982:64–75 Groups, J. Arthroplasty, 1993; 8:315–22.

Hildreth E, *Edge Detection*, In: Shapiro S, ed. Encyclopedia of Artificial Intelligence, Wiley, New York 1987 257–67.

Bland JM, Altman DG, *Statistical Methods for Assessing Agreement Between Two Methods of Clinical Measurement*, Lancet, 1986; 2:307–10.

Kabo JM, Gebhard JS, Loren G, Amstutz HC, *In Vivo Wear of Polyethylene Acetabular Components*, The Journal of Bone and Joint Surgery, Inc., 1993; 75–B:254–8.

Marel E, Unpublished Data Presented at 1994 A.A.O.S. meeting, New Orleans, LA.

Davy DT, Kotzar GM, Brown RH, Heiple KG, Goldberg VM, Heiple KT, Jr, Berilla J, Burstein AH, *Telemetric Force Measurements Across the Hip After Total Arthroplasty*, The Journal of Bone and Joint Surgery, Inc., 1988; 70–A(1); 45–50.

Wright TM, Rimnac CM, *Analysis of Retrieved Polyethylene Components from Total Joint Replacements*, Department of Biomechanics, pp. 202–207. No date.

METHOD AND DEVICE FOR LINEAR WEAR ANALYSIS

REFERENCE TO COMPUTER PROGRAM APPENDIX

A computer program appendix, comprising a total of 63 pages of computer object codes listing in hexadecimal format with a single title page, is attached hereto as Appendix A, and is hereby incorporated by referenced into this application as if fully set forth herein. The program being used in conjunction with VICTOR LIBRARY, produced by Catenary Systems, 470 Belleview, St. Louis, Mo.

AUTHORIZATION TO COPY COMPUTER PROGRAM APPENDIX

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

1. Field of the Invention

The present invention generally relates to a method and apparatus for analyzing radiographic images to determine the wear in a liner between a bearing and a bearing cup or housing and more particularly to a method and apparatus for analyzing radiographic images of a prosthetic hip replacement to determine the wear between a femur component and a liner of an acetabular component forming parts of the prosthetic hip replacement.

2. Background of the Invention

It is often necessary to reduce the friction between a bearing having a generally spherical surface and a housing for the bearing by the placement of a low friction liner on the inner surface of the housing and between the housing and bearing. But, movement of the bearing relative to the liner and the force applied by the bearing on the liner may cause the liner to wear.

In total hip arthroplasties, a polyethylene liner is placed on an inner surface of an acetabular cup forming a part of the arthroplasty to reduce friction between the cup and a femur bearing at the upper end of the femur component also forming a part of the arthroplasty. Wear of this polyethylene liner produces polyethylene debris. The polyethylene debris has recently been implicated as a cause of prosthetic loosening and subsequent failure in total hip arthroplasty prosthetic replacements. Research has found that polyethylene wear is three times greater in failed prosthetic hip joints than in joints which are still operational, suggesting a casual relationship between wear and loosening. Although the reason for this loosening and the details of the actual mechanism of loosening are still under investigation, polyethylene debris resulting from the wear is thought to be a major contributing factor.

Although polyethylene wear rates for total hip arthroplasties are small, ranging from 0.1 mm to 0.2 mm/year, even small amounts of polyethylene wear generate millions of submicron polyethylene particles. This debris may elicit a foreign-body tissue reaction followed by osteolysis, osteoclasia and secondary fibroplasia at bone-implant interfaces resulting in prosthetic loosening. In cases of excessive wear, hip range of motion may be reduced to the extent that femoral component impingement against the rim of the acetabular component results in increased acetabular loosening.

Currently, the association between polyethylene wear, osteolysis, and subsequent prosthetic failure are of primary concern in orthopaedics and biomaterial research. Postmortem examination or analysis of hip prosthesis does not provide sufficient numbers for an accurate determination of polyethylene wear rates in the general population. Also, as is obvious, invasive procedures to measure the wear are not practical. As such, the accurate, non-invasive determination of polyethylene wear in situ is critical.

Currently one non-invasive technique to provide such an in situ wear determination is to compare radiographs taken shortly after implantation or "post-op" radiographs with radiographs taken months or even years later. Several investigators have developed manual techniques for the determination of polyethylene wear by comparing clinical radiographs. However, such manual examinations have drawbacks.

One primary drawback is that the reproducibility of the measured wear is low. For example, one investigator using such a technique may make one wear determination from a particular pair of radiographs, while a second investigator may make a substantially different wear determination from the same pair of radiographs. Even reproducibility of the wear determination by the same investigator has been found to be low. This lack of reproducibility hinders research into the correlation between wear and prosthetic failure.

Another drawback is that the manual technique is very slow. The technique generally involves seeking to discern edges and centers of the arthroplasty components by fitting curves and lines on the radiographic edges and images. After the curves and lines are placed on the radiographs, measurements are made to determine wear. The time required to perform these steps hinders the ability of the user to make wear determinations of a large sample of patients. A related drawback is that typically edges of the components on a radiographic are hard to exactly discern and discerning an exact edge is very important in making a wear determination.

Therefore an object of the present invention is to provide an improved non-invasive technique for more accurate and reproducible analysis of wear in the liner between a rotary bearing type component and the bearing housing. A related object is to provide such an improved technique which analyses the wear in the liner between the femur component or bearing and an acetabular cup of a hip arthroplasty.

A further object of the present invention is to provide an improved technique for quickly determining the wear in the liner between the femur bearing and acetabular cup while minimizing the number of manual steps which need to be made to make such a determination.

SUMMARY OF THE INVENTION

Accordingly a method and apparatus are disclosed for determining the wear of a liner separating a rotatable bearing from a generally spherical housing. The method includes digitizing a first radiographic image of the bearing and housing after some period of use and processing elements making up the image to define and locate the centers of the bearing and housing within the image. The process is also undertaken for a second radiograph image of the bearing and housing taken soon after installation/implantation. Then a determination is made of the movement of the center of the bearing relative to the center of the housing during the time period between when the first radiographic image was made and when the second radiographic image was made. The distance of such movement being related to the wear of the liner.

More particularly, in determining the wear of a liner between a femur component and an acetabular component or cup of a total hip arthroplasty, a method is provided which includes:

(a) digitizing into an image made up of a plurality of elements, a first radiograph of at least a portion of the femur component and acetabular cup; (b) smoothing at least a portion of the elements to reduce spurious intensity changes among the elements; (c) directionally accenting the smoothed elements to highlight a first edge gradient of the femur component and a second edge gradient of the acetabular cup; (d) defining at least a portion of an edge of the femur component within the first edge gradient and defining a center of the femur component; (e) defining at least a portion of an edge of the acetabular cup within the second edge gradient and defining a center of the acetabular cup; (f) determining a first vector extending from the center of the acetabular cup to the center of the bearing; (g) undertaking steps (a)–(f) for a second radiograph, taken after the first radiograph, and determining a second vector extending from a center of the acetabular cup to a center of the bearing; and (h) mapping the first vector and the second vector extending together and determining a wear vector from the first vector to the second vector.

BRIEF DESCRIPTION OF THE DRAWINGS

FIG. 4 is an enlarged portion of the pictorial representation of FIG. 4a;

DESCRIPTION OF THE PREFERRED EMBODIMENT

Figure 1:
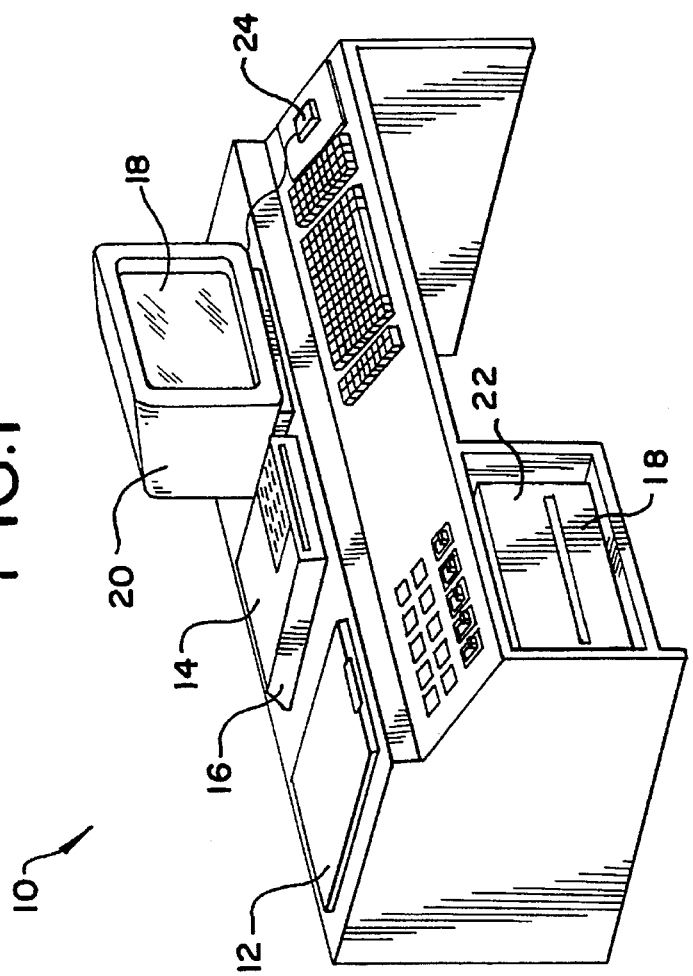
FIG. 1 is a preferred embodiment of an apparatus for digitizing and processing a radiograph in accordance with the preferred method of the present invention.

Referring to FIG. 1, a preferred embodiment of an apparatus for making wear measurements in accordance with the preferred method of the present invention is generally indicated at 10. The apparatus 10 preferably includes a high resolution scanner 12 such as a laser scanner having a pixel size of 0.171 mm×0.171 mm and a matrix size of 2000× 2430. The apparatus 10 also includes a digital computer 14, such as the shown desktop personal computer 16, for analyzing the digital image provided by the scanner 12; and an output device 18. The output device 18 preferably includes a monitor 20 such as a high resolution monitor and may also include a printer 22, again preferably high resolution. The digital computer 14 should include a mouse 24 or other device for providing input to the computer by clicking on particular locations of an image displayed on the monitor 20.

Figure 2:
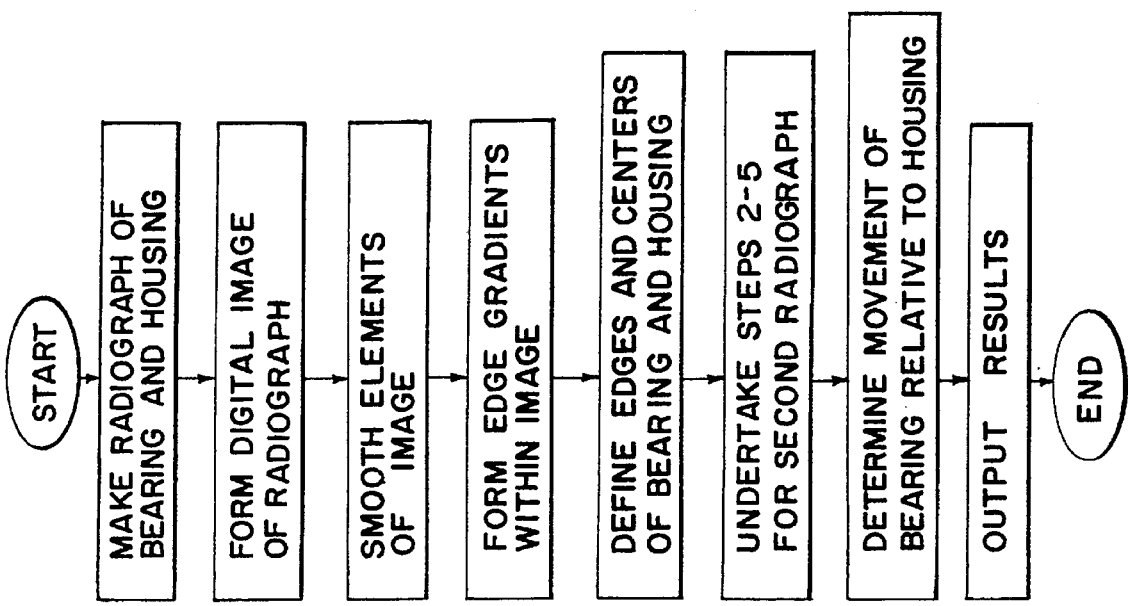
FIG. 2 is a flow diagram illustrating a preferred method of the present invention.
Figure 3:
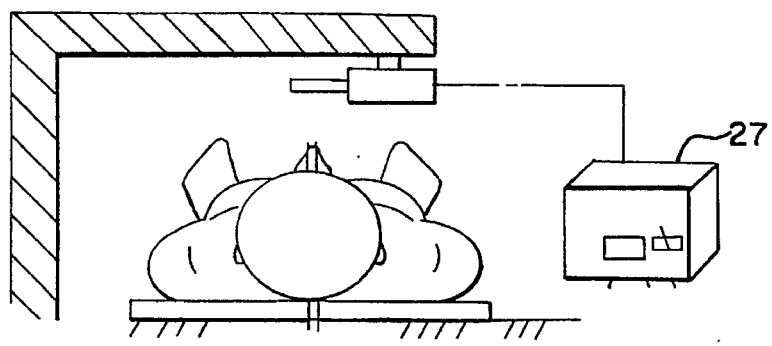
FIG. 3 is a diagrammatic view of the taking of a radiograph.

Referring to FIGS. 2 and 3, in measuring wear, a radiograph 26 is taken of a particular region of the body which contains the object of interest. The radiograph 26, such as a pelvis radiograph, is typically created through the use of x-rays originating from an x ray device 27, with the rays passing through a body such as the human body which contain the components which may be subject to wear. The rays impinge on a negative 26a or the like so that an image of structures, contained within the particular region of interest, is formed non-invasively. It is contemplated that radiographs 26 can also be made using gamma rays or other body penetrating rays.

Figure 4:
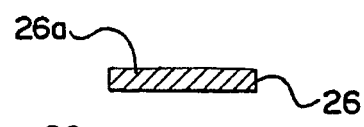
Figure 4:
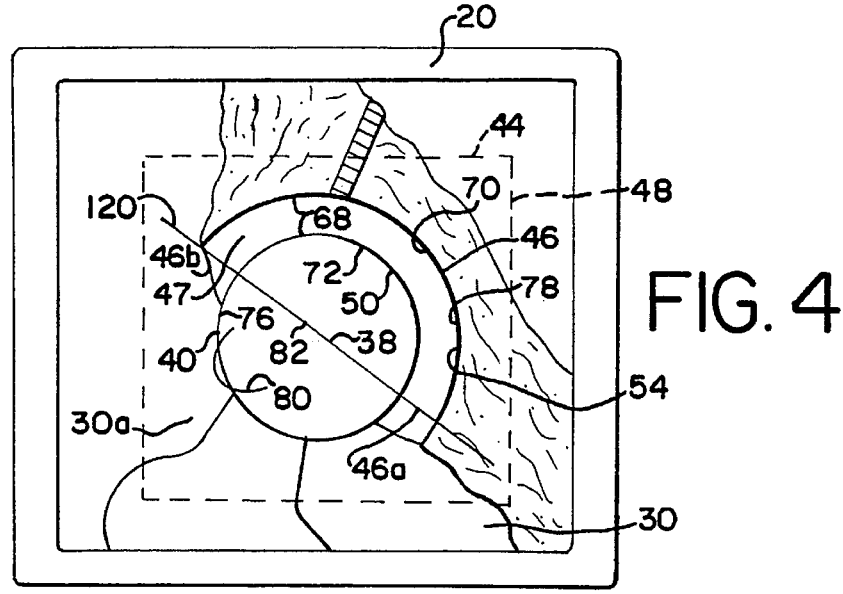
Figure 4A:
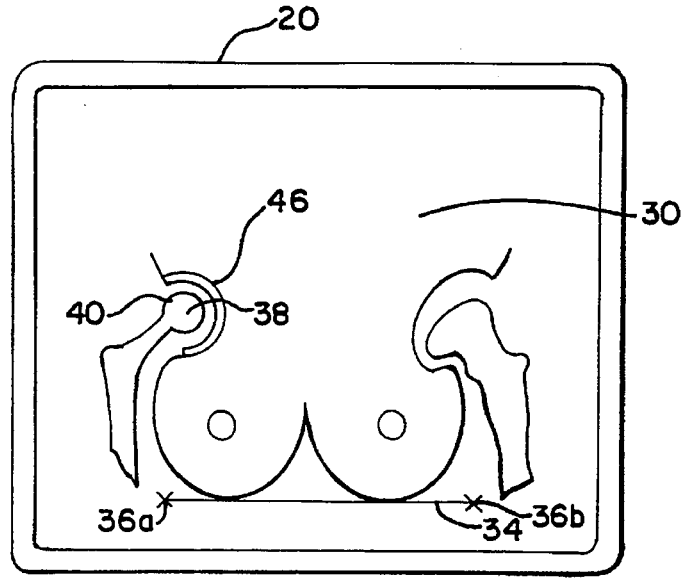
FIG. 4a is a pictorial representation of a digital image displayed on a monitor forming a part of the apparatus of FIG. 1.

Referring to FIGS. 1 and 2, the resulting radiograph 26 (FIG. 3) or negative 26a is placed on the scanner 12 and digitized by scanning. Preferably, the scanner 12 digitizes the radiograph 26 into a 256 shade 10 bit grey scale image having a pixel 28 (FIG. 5) size of 0.171 mm×0.171 mm and a total matrix size of 2000×2430 pixels 28. Once digitized, the 10-bit image may be converted to an 8-bit image using histogram equalization. This transformation procedure minimizes the loss of contrast information in the image during gray level reduction. Referring also to FIGS. 4 and 4a, the image is then preferably converted into a Tag Image File Format (TIFF) image 30, a universal image format supported by many software programs. The radiograph 26 (FIG. 3) may also be digitized directly into an 8 bit image 30 and may be utilize other formats such as GIF, JMEG or the like. It is also envisioned that a radiograph 26 may be directly converted into the digital image 30 without the use of negatives and scanners or the like.

The digitized image 30 is then displayed on the monitor 20 and an image reference line 34 is defined by the user by interactively clicking with the mouse on two points such as points 36a, 36b within the image 30. To correspond with common practice, a line tangent to the ischial tuberosities is preferably defined as the reference line 34.

Referring in particular to FIG. 4 which is a view of a portion of the image 30, enlarged for clarity, an approximate center 38 of a prosthetic head or femur bearing 40 forming a part of a total hip arthroplasty 42 is then designated by an interactive click of the mouse 24 (FIG. 1). The designation of the approximate center 38 anchors a Region of Interest (ROI) 44 of the image 26. The computer 14 (FIG. 1), operating under an automatic image analysis program set forth in Appendix A, then defines the ROI 44 so as to include depictions of a number of the prosthetic joint components such as the femur bearing 40, an acetabular cup 46 and a separating liner 47. The ROI 44 is then extracted from the image 26. The ROI 44 is typically defined and extracted by setting boundaries 48 of the ROI 44 at a distance from the designated center 38 which is greater than the designed distance of the prosthetic joint components from the true center of the femur bearing. The ROI 44 is preferably shaped with boundaries 48 in the form of a rectangle to facilitate the manipulation of the data contained therein.

Figure 5:
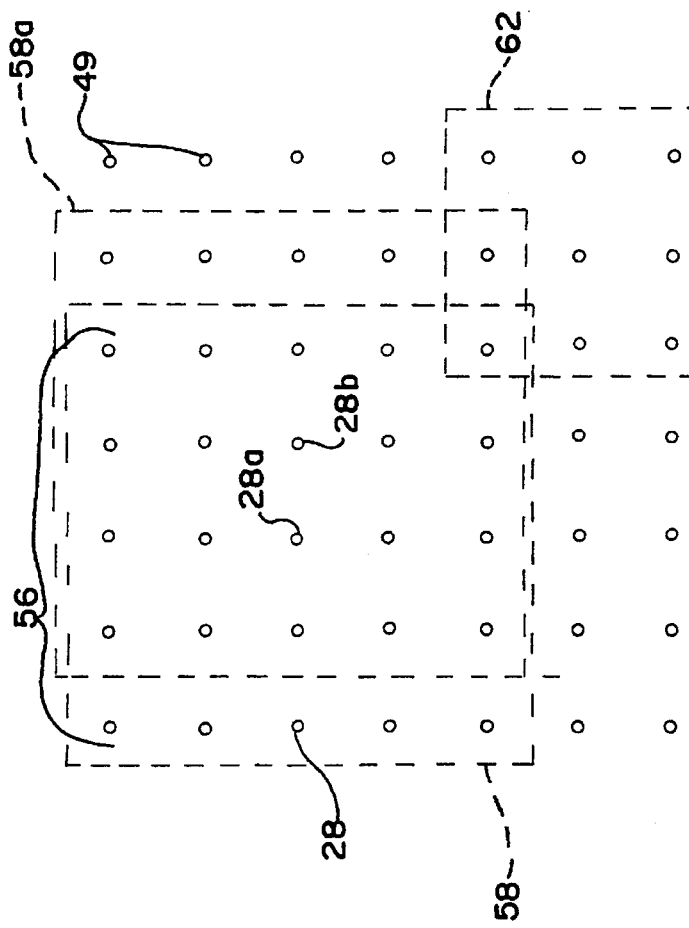
FIG. 5 is a diagrammatic sketch of a greatly enlarged view of a subset of elements making up the image of FIG. 3.

Referring also to FIG. 5, in ascertaining the wear, the accurate determination of dimensions and spacing of the edges of the various prosthetic components depicted in the image 30 becomes very important. In typical radiographs 26, the edges of the components are indicated by changes in the shading or intensity of elements 49 making up the radiograph 26. However, the shading changes are frequently fuzzy and the exact edge may be difficult to determine. This inability to determine exact edges may seriously hinder the determination of wear. Thus, in the preferred method of determining wear, a portion 30a of the image 30, contained within the ROI 44, is refined, enhanced or converted to define within the image 30, an edge 50 of the femur bearing 40, an edge 54 of the acetabular cup 46, and the surrounding bone.

General procedures for making and enhancing digital images are described in Ballard DH, Brown CM, *Computer Vision,* Englewood Cliffs, N.J., Prentice-Hall, 1982:64–75, and Hildreth E, Edge Detection, *Encyclopedia of Artificial Intelligence,* Wiley New York 1987, 257–67, hereby incorporated by reference. In the digital image 30, the elements 49 of the image are represented by the value of the pixels 28. One of the first steps in the image conversion process smoothes the values of the pixels 28 in order to reduce the effect of noise and fine texture on the detection of intensity changes among generally adjacent pixels, such intensity changes frequently represent edges. This reduction is necessary as the sampling and transduction of light introduces spurious changes of light intensity among adjacent pixels 28 that do not correspond to significant, physical changes as depicted in the image 30.

In particular, individual pixels 28a within the ROI are smoothed using a normalizing or smoothing function applied to a subset of pixels 28 within a general proximity of the pixel 28a. Preferably, a 5×5 matrix 58 of pixels 28 is selected with the pixel 28a being smoothed placed in the center of the matrix and a smoothing function, such as the following two-dimensional Gaussian smoothing function, is applied to the pixel values, $$G(x,y,\sigma) = \frac{1}{2\Pi\sigma^2} e^{(-\frac{x^2+y^2}{2\sigma^2})}$$

where σ is the standard deviation and x and y are the coordinates of the pixel 28 relative to pixel 28a, such that the sum of the matrix 58 is 1.0.

A second subset 56 is then selected, preferably by forming a second 5×5 matrix 58a displaced laterally by a column from the first matrix 58 and the smoothing function is applied to a second pixel 28b. The matrix 58 forming may be continued until all the pixels 28 within the ROI 44 are smoothed.

Figure 6:
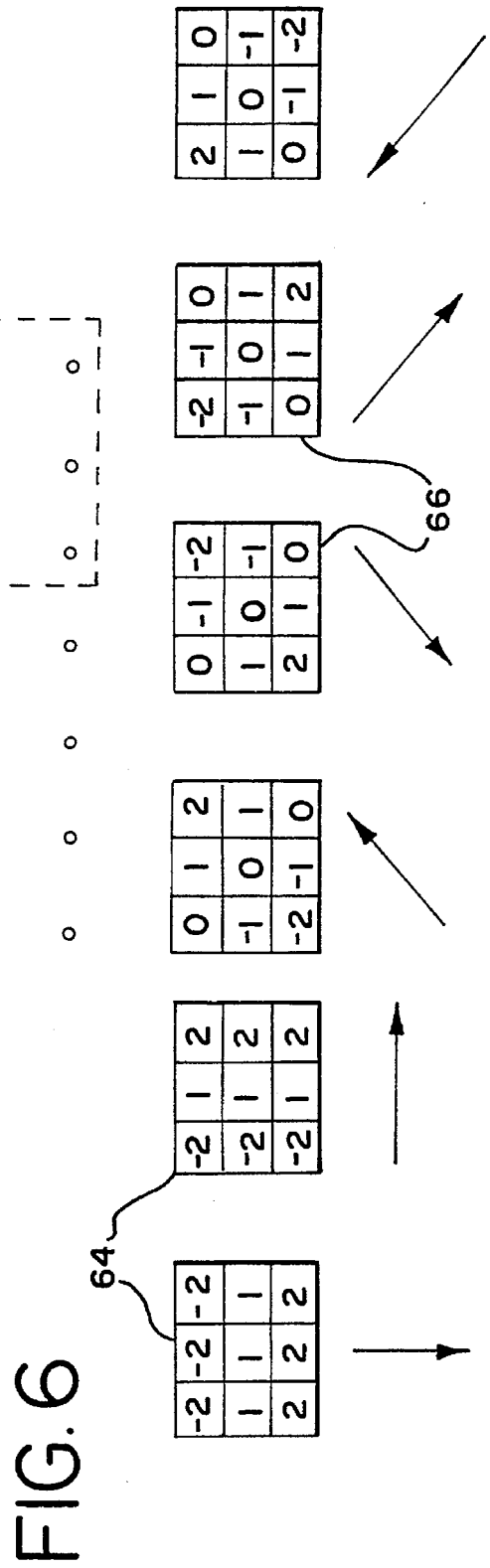
FIG. 6 illustrate operators for forming edge gradients in the image of FIG. 4 with accompanying arrows representing edge gradient detection directions.

The next step of the image analysis accentuates the intensity changes between smoothed, adjoining pixels 28 of the image 30, transforming the image 30 into a representation such that higher pixel 28 values more likely correspond to distinct edges of the images of components within the ROI. Referring to FIGS. 5 and 6, preferably for this transformation, the values of subset 3×3 pixel matrixes 62 are multiplied by at least one 3×3 directional Sobel operator 64. The Sobel operator is preferably used because of the sensitivity of the operator in detecting low intensity edges in an image 30 (FIG. 4) and in the simplicity of the operator. The Sobel operators 64 are defined and convolve with the image 30 to detect edges in vertical (up, down) and horizontal (right, left) directions. The image 30 is also convolved with four additional diagonal operators 66, modeled after the Sobel operators, to detect edges in corresponding diagonal directions 67.

Referring to FIG. 4 in conjunction with FIG. 6, after convolution of the image 30 within the ROI 44 with one of the operators 64, 66, a high pixel value corresponds to a greater chance that the pixel 28 represents one of the elements of the image of a portion of a physical edge which extends generally normal to the direction of the operator 64, 66. Generally high values of several adjacent pixels or edge gradients 68 are formed by the operators 66, 68.

Because the operators 64, 66 are generally sensitive in only one direction, several operators are used to form individual edge gradients 68 within the ROI with the individual gradients stored in an accumulator in the computer 24. To provide complete coverage of the acetabular cup 46, which produces a generally curved image of constant radius extending roughly 180 degrees, individual edge gradients 68 in five directions are calculated and then summed to produce a first total edge gradient 70, one of two edge gradient. A second total edge gradient 72 is computed for the femur bearing 40. Because the curved edge of the femur bearing is generally extends 270 degrees, six operators 64, 66 are typically used. The directions selected are dependent on the side of hip (right or left) being analyzed. Whether the image is of the right or left hip is usually determined by the user designation of the approximate center 38 of the femur bearing 40 relative to the total image 30 of the radiograph, as shown in FIG. 4a.

Referring back to FIG. 4, once the first total edge gradient 70 and second total edge gradient are 72 produced, the edge 50 of the femur bearing 40 is defined with an arc 76 which best predicts the image of the actual edge of the femur bearing on the image 30. The edge 54 of the acetabular cup 46 is defined within an arc 78 which best predicts and fits the edge 54 of the acetabular cup on the image. The arcs 76, 78 may be produced using the Hough technique for curve detection. Because the edges 50, 54 are generally circular, preferably the Hough technique is constrained to produce an arc of constant radius. To compensate for implantation techniques and orientation of the pelvis during the taking of the radiographs, arcs 76, 78 of approximately 225 degrees are used.

The definition of the edge 50 of the preferably defined first. In producing the best fit arc 76, arcs 80 of constant radius having different centers and which pass through a selected pixel are formed. Each pixel, for example 28a (FIG. 5), within a desired examination area is individually examined as a potential pixel within the best fit arc 76, and the arcs 80, which pass through the examined pixel, being formed with various possible radiuses.

For each formed arc 80 of a given radius, the pixels in the arc 80 "votes" for the pixel 28 at the center of curvature of the arc which may represent the valid center of the femur bearing 40 with the "vote" equal to the pixel value (summed edge value). To reduce processing time, the ROI 44 is reduced four fold thereby reducing the number of examined pixels 28. Also, pixels 28 which may correspond to the valid center of the femur bearing 40 are preferably constrained within a range of possible centers. For the femur bearing 40, the range of possible centers for the valid center is from the approximate center 38, defined earlier, to the known diameter of the femur bearing 40.

Referring also to FIG. 6, for each formed arc 80, the votes of pixels 28 along the arc are summed or totalled. This "voting" process is repeated for all pixels 28 which are a part of arcs 80 having a valid center within the constrained range. The pixel 28 representing a center 82 of the femur bearing 40 and arc 76 which best defines the edge 50 are determined by which pixel 28 and arc 80 received the largest number of votes.

To better define the edge 50 and center 82, the image 30 is then restored to the original size and the arc 80 forming process is repeated with the possible valid centers and examined pixels 28 being constrained within areas closely adjoining the center 82 and arc 76 defined in the reduced image. The edge 50 and center 82 are then redetermined by the voting process in the original sized image 30. If the reduction/restoration process does not appear to obtain a satisfactory edge 50, the reduction step may be manually overridden and the arc forming process may be applied to all the possible pixels on the original sized image.

A similar process is repeated to determine, from the pixels 28 in the edge gradient 72, the arc 78 which best defines the edge 54 and center 86 for the acetabular cup 46. In determining the center, the range of valid centers for the acetabular cup includes the found prosthetic head center 82 and extends to the maximum wear possible or the size of the femur bearing and the initial thickness of the liner 47.

The definition of edges 50, 54 with arcs 76, 78 may be manually modified if satisfactory results are not produced. The range of valid centers and radii range, may be limited by clicking, for arc 78, on three points, on for arc 72, what appears to be the edge gradient of the acetabular cup 46 in the image 30, or for arc 76, what appears to be the edge gradient 74 of the femoral bearing 54.

The arc 76 defines the image of the edge 50 of the femur bearing 40 and the arc 78 defines the image of the edge 54 of the acetabular cup 46. Once the image of the edge 50 of the femur bearing 40 has been defined, distances between the various components depicted on the image 30 may be correlated with actual distances of the hip arthroplasty. In order to convert pixel distances within the image 30 to millimeters on the hip arthroplasty, a correction factor, which is equal to the known diameter of the femur bearing (mm) divided by a calculated diameter of the image of the femur bearing 40 (pixels), is applied. In addition, all angles are expressed with the drawn ischial tuberosity reference line 34 as representing the 0°–0° or horizontal axis.

The center and edge detection process is also undertaken for a radiograph taken shortly after the installation of the prosthetic component or "post-op" radiograph, to determine the initial positions of center 82' of the femoral bearing 40 and the center 86' of the acetabular cup 46. The post-op radiograph may be digitized or the digital image of the radiograph may already be stored in memory. Although the post-op radiograph is preferably analyzed after the latest radiograph, the sequence can be easily reversed.

The movement of the bearing 40 relative to the cup 46 which correlates to the wear of the separating liner 47 is then determined. In the preferred embodiment, the movement is determined by calculating in the post-op image 30 a first vector 90 extending from the determined center 86 of the acetabular cup 46 to the center 82' of the bearing 50. A similarly extending second vector 92 is calculated for the latest image 30. As shown in FIG. 6, one of the first or second vectors 90, 92 may then be mapped onto the coordinate system of the other of the first or second vectors 90, 92 with the vectors extending out from a common point, i.e., the found center 86 of the acetabular cup 46, a third vector or wear vector 94 extending from a head or point 90a of the first vector 90 to a head or point 92a of the second vector 92 may then be calculated. The third vector represents a projection along the plane of the radiograph 26 (FIG. 3) of the magnitude and direction of the movement of the femur bearing 40 relative to the cup 54 in the time period between the post-op radiograph and the recent radiograph and thus the wear of the liner 88. The magnitude and direction may be outputted in a window on the monitor 20 or via printer 22.

Figure 7:
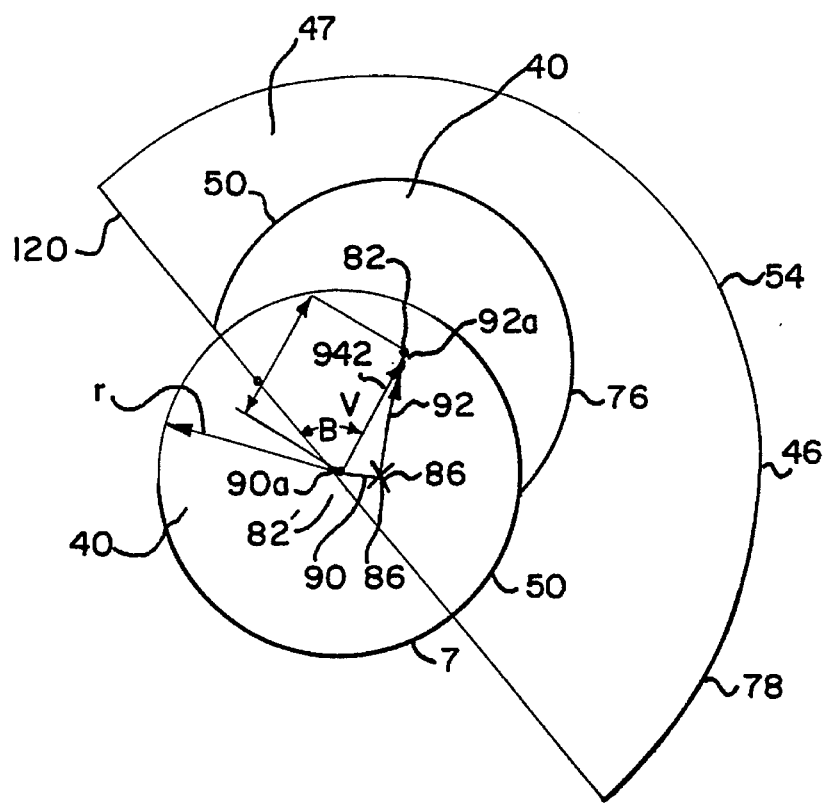
FIG. 7 is an image which may be formed over the pictorial representation of FIG. 4 in accordance with a preferred method of the present invention, the representation being removed for clarity.
Figure 8:
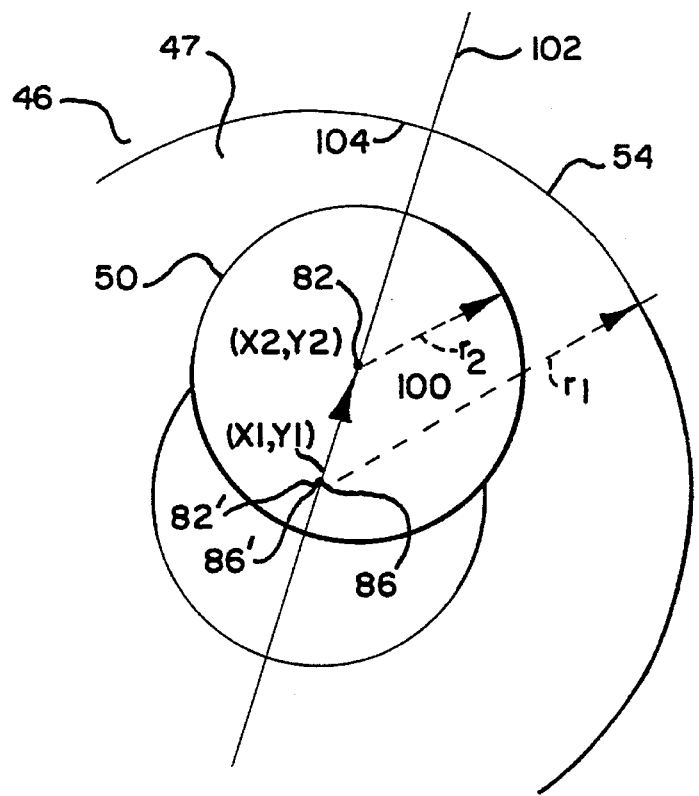
FIG. 8 is a sketch of a second image which may be formed in accordance with an alternate method of the present invention.

Referring to FIG. 7, a second, less preferred technique of calculating the wear is to first assume that, when the prosthetic components 39 were first implanted, the center 82 of the femoral bearing 40 and the center 86 of the acetabular cup 46 occupied the same point. Then the edge 54 and center 86 of the acetabular cup 46 and the edge 50 and center 82 of the femur bearing 50 are determined from the image 30 of the most recent radiograph 26 using the process described above. The minimum thickness (d1) of the liner 47 on the most recent image 30 is determined by the following formula:

$$r1 - r2 - \sqrt{(y2-y1)^2 - (x2-x1)^2}$$

Where r1 is the radius of the acetabular cup 46, r2 is the radius of the femur bearing 40, x1,y1 is the position of the center 86 of the acetabular cup 46 and x2,y2 is the position of the center 82 of the femur bearing 40. It also follows that in this analysis the direction of the minimum thickness of the liner 88 is the direction of a vector 100 from the center 86 to the center 82.

The initial thickness of the liner 47 is then determined. The relative directions between the images 30 of the post-op radiograph 26 and recent radiograph are correlated using the reference line 34 (FIG. 4). On the post-op radiograph, the center 82' and edge 50' of the femur bearing 40 and edge 54 of the acetabular cup 54 are then determined. An equation of a line 102 extending through the center 82 and having the slope of the vector 100 is determined. A point 104 of intersection of the line 102 and the edge 54 of the acetabular cup 46 is determined using the equation of the line 102, an equation of a circle representing the edge 54 and solving using the quadratic formula. Knowing the radius r2 of the femur bearing 50, the initial thickness of the liner 47 is then the distance from the center 82 to the intersection point 104 minus the radius r2. The wear is then the initial thickness minus the minimum thickness.

Determining the thickness of the liner 47 under the assumption that the center 82 and center 86 initially occupied the same point is not as desirable as this assumption is not correct for many prosthetic implants where the initial position of the centers do not coincide. Thus the determination based on this assumption may understate or overstate the degree of wear.

Referring to FIGS. 1 and 4, the determined amount and direction of movement of the femur bearing relative to the acetabular cup may be outputted by graphical representation on the image 30, or the output may be directed to the printer 22. Also the defined edge 50 of the femur bearing 40 and the defined edge 54 of the acetabular cup 46 may be mapped on the image 30. With the mapping, the user may discern whether the results are satisfactory or whether a manual override may be needed.

Once the wear vector 94 is obtained volumetric wear of the liner 47 can also be determined. To determine volumetric wear, an inclination angle reference line 120 may be defined, by clicking within the image 30, on the inferior edge 46a and superior edge 46b of the acetabular cup 46. The amount of volumetric wear (V) is dependent on the direction and distance (d) of the movement of the femur bearing 40 into the liner 47, and on the radius (r) of the femur head according to the following formula:

$$V = \Pi r^2 d - r^2 \left[ d\cos^{-1}\left(\frac{d\tan(\beta)}{r}\right) - \sqrt{\frac{r^2}{\tan^2(\beta)} - d^2} + \frac{r}{\tan(\beta)} \right] - \frac{r^3}{3\tan(\beta)} \cdot \left[ \left(1 - \frac{d^2\tan^2(\beta)}{r^2}\right)^{3/2} - 1 \right]$$

Where, angle $\beta$ is the angle between the wear vector 94 and the inclination angle reference line 120.

A specific embodiment of the novel total hip polyethylene wear analysis program according to the present invention has been described for the purposes of illustrating the manner in which the invention may be made and used. It should be understood that implementation of other variations, and modifications of the invention in its various aspects will be apparent to those skilled in the art, and that the invention is not limited by the specific embodiment described. It is therefore contemplated that the present invention covers any and all modifications, variations, or equivalents that fall within the true spirit and scope of the basic underlying principles disclosed and claimed herein.

What is claimed is:

1. A method for determining the wear of a liner separating a rotatable bearing from a generally spherical housing, comprising the steps of:
   (a) digitizing into an image made up of a plurality of elements, a first radiograph of at least a portion of the liner, bearing and housing;
   (b) smoothing at least a portion of elements making up the image;
   (c) directionally accenting the elements to highlight a first edge gradient of the bearing and a second edge gradient of the housing;
   (d) defining at least a portion of an edge of the bearing by fitting a first arc among the accented elements and defining a center of the bearing;
   (e) defining at least a portion of an edge fitting by an arc by fitting a second arc among the accented elements and defining a center of the housing;
   (f) determining a first vector from the center of the housing to the center of the bearing;
   (g) undertaking steps (a)–(f) for a second radiograph, taken after the first radiograph, to determine a second vector from the center of housing to a center of a bearing on the second radiograph;
   (h) mapping the first vector and the second vector together and determining a wear vector from the first vector to the second vector.

2. A method of non-invasively determining the wear in a liner disposed between a femur component and an acetabular component of a hip arthroplasty, comprising the steps of:
   (a) obtaining a digitized radiographic image of the hip arthroplasty containing an image of the femur component and an image of the acetabular component;
   (b) smoothing at least a portion of elements making up the radiographic image;
   (c) defining edges of the femur component image and the acetabular component image, the defining step including forming an edge gradient for the femur component image and an edge gradient for the acetabular component image and fitting an arc within each of the edge gradients, the arcs representing the edges of the femur component image and the acetabular component images,
   (d) determining centers of the femur component image and the acetabular component image and the distance separating the centers;
   (e) determining the location and length of the shortest distance between the edge of the femur component image and the acetabular component image; and
   (f) determining an original thickness of the liner.

3. The method of claim 2 wherein the original thickness determination step includes undertaking the steps (a)–(c) for a second digitized radiographic image of the hip arthroplasty containing an image of the femur component and an image of the acetabular component.

4. A method of non-invasively determining the wear in a liner disposed between a femur component and an acetabular component of a hip arthroplasty, comprising the steps of:
   (a) obtaining a digitized radiographic image of the hip arthroplasty containing an image of the femur component and an image of the acetabular component;
   (b) smoothing at least a portion of elements making up the radiographic image;
   (c) directionally accenting the smoothed elements and highlighting an edge gradient for the femur component image and an edge gradient for the acetabular component image;
   (d) determining a center of the femur component image, the determining step including fitting a first arc among the accented elements, the first arc representing at least a portion of an edge of the femur component image;
   (e) determining a center of the acetabular component image, the determining step including fitting a second arc among the accented elements, the second arc representing at least a portion of an edge of the acetabular component image;
   (f) determining a first vector from the center of the acetabular component image to the center of the bearing component image;
   (g) undertaking steps (a)–(f) for a second radiograph, taken after the first radiograph, to determine a second vector from the center of the acetabular component image to the center of the bearing component image on the second radiograph;
   (h) mapping the first vector and the second vector together and determining a wear vector from the first vector to the second vector.

5. The method of claim 4 further including reducing the size of the portion of the image formed by the directionally accented elements, before determining a center of the femur component and acetabular component.

6. The method of claim 4 wherein the directional accenting includes multiplying values of the elements by directional operators.

7. The method of claim 4 wherein the smoothing step includes selectively forming a plurality of matrices of adjoining elements and applying a smoothing function to the elements in the matrix to determine a smoothed value of an least one of the elements in the matrix.

8. An apparatus for non-invasively determining the wear in a liner disposed between a femur component and an acetabular component of a hip arthroplasty, comprising:
   means for digitizing a first radiographic image of the hip arthroplasty, the first image containing an image of the femur component and an image of the acetabular component; and
   means for;
      smoothing at least a portion of elements making up the radiographic image, directionally accenting the smoothed elements and highlighting an edge gradient for the femur component image and an edge gradient for the acetabular component image, determining a center of the femur component image by fitting a first arc among the accented elements, the first arc representing at least a portion of an edge of the femur component image, determining a center of the acetabular component image, by fitting a second arc among the accented elements, the second arc representing at least a portion of an edge of the acetabular component image, determining a first vector from the center of the acetabular component image to the center of the bearing component image, determining a second vector from a center of the acetabular component image to a center of the bearing component image on a second digitized radiographic image of the hip arthroplasty taken before the first radiographic image, and mapping the first vector and the second vector together and determining the magnitude and direction of a wear vector from the second vector to the first vector.

9. The apparatus of claim 8 further including means for outputting the direction and magnitude of the wear vector.

10. The apparatus of claim 9 wherein said outputting means includes a monitor.

11. The apparatus of claim 8 wherein said digitizing means includes a scanner.

12. The apparatus of claim 8 wherein the first means includes a digital computer configured to perform the smoothing, accenting, determining and mapping functions.

13. The apparatus of claim 8 including means for displaying the digitized radiographic image.

14. The apparatus of claim 13 including means for identifying selected locations on the digitized image displayed on the displaying means.

15. The apparatus of claim 14 wherein the identifying means includes a mouse.

16. The apparatus of claim 8 including means for obtaining the first radiographic image.

17. A method for determining the wear in a liner disposed between a bearing component and a housing component of an implanted replacement arthroplasty, comprising the steps of:

determining the relative position of the bearing component and acetabular component at a first, period of time by non-invasively determining the length and orientation of a first vector extending from a center of the bearing component to a center of the housing component;

determining the relative position of the bearing component and acetabular component at a second period of time after the first period by non-invasively determining the length and orientation of a second vector extending from the center of the bearing component to the center of the housing component; and mapping the first vector and second vector together and determining the length and orientation of a third vector extending between a point on the first vector and a point on the second vector.

* * * * *